US00PP24663P3

(12) United States Plant Patent
Brazelton et al.

(10) Patent No.: US PP24,663 P3
(45) Date of Patent: Jul. 22, 2014

(54) BLUEBERRY PLANT NAMED 'OVERTIME'

(50) Latin Name: *Vaccinium virgatum*
Varietal Denomination: Overtime

(75) Inventors: David M. Brazelton, Walterville, OR (US); Adam L. Wagner, Eugene, OR (US)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 150 days.

(21) Appl. No.: 13/385,904

(22) Filed: Mar. 12, 2012

(65) Prior Publication Data

US 2013/0239262 P1 Sep. 12, 2013

(51) Int. Cl.
*A01H 5/00* (2006.01)

(52) U.S. Cl.
USPC ..... Plt./157

(58) Field of Classification Search
CPC ..... A01H 5/08
USPC ..... Plt./157
See application file for complete search history.

*Primary Examiner* — June Hwu
(74) *Attorney, Agent, or Firm* — Davis Wright Tremaine LLP; Dale C. Hunt; Wenhua Yu

(57) ABSTRACT

The new blueberry plant variety 'Overtime' is provided. 'Overtime' is a commercial variety intended for the hand harvest fresh market. The variety has medium sized, light blue fruit which has and an excellent fruity flavor and lacks the typical grittiness of rabbiteye blueberries. The variety shows good tolerance to bacterial canker caused by *Pseudomonas syringae.*

3 Drawing Sheets

Latin name of the family, genus, and species: Family—Ericaceae. Genus—*Vaccinium.* Species—*virgatum.*

Variety denomination: The new blueberry plant claimed is of the variety denominated 'Overtime.'

CROSS REFERENCE TO RELATED APPLICATIONS

None.

STATEMENT REGARDING FEDERALLY-SPONSORED RESEARCH AND DEVELOPMENT

None.

BACKGROUND OF THE INVENTION

The present invention relates to the discovery of a new and distinct cultivar of rabbiteye blueberry known as a *Vaccinium virgatum* referred to as 'Overtime,' as herein described and illustrated.

The new blueberry plant variety 'Overtime' was selected in Lowell, Oreg. in 2006. 'Overtime' is a commercial variety intended for the hand harvest fresh market. The variety has medium sized, light blue fruit which has an excellent fruity flavor and lacks the typical grittiness of rabbiteye blueberries. 'Overtime' ripens about one week earlier than 'Powderblue' and 'Ochlockonee' (U.S. Plant Pat. No. 17,300), and has comparable yields. The variety shows good tolerance to bacterial canker caused by *Pseudomonas syringae.*

Pedigree and History: The new blueberry plant originated from a cross of 'Centurion' (female parent, unpatented) by 'Powerblue' (pollen parent, unpatented). The new blueberry plant variety 'Overtime' has been planted in replicated trials since 2007.

The new variety can be compared to commercial variety 'Ochlockonee' in that 'Overtime' has larger berries and ripens about one week earlier.

The new variety can be compared to commercial variety 'Powerblue' in that 'Overtime' has larger berries with better flavor, and ripens about one week earlier.

The new blueberry plant variety 'Overtime' has maintained its distinguishing characteristics throughout successive asexual propagations. The variety has been repeatedly asexually reproduced through softwood cuttings in Lowell, Oreg., and the clones are phenotypically identical to the original plant.

SUMMARY OF THE INVENTION

The new blueberry plant variety 'Overtime' has not been observed under all possible environmental conditions. The phenotype may vary somewhat with variations in environment and cultural practices such as temperature and light intensity without, however, any variance in genotype.

The following traits have been repeatedly observed in Lowell, Oreg., and are determined to be the unique characteristics of the new blueberry plant variety 'Overtime':

1. Medium sized, round fruit with excellent fruity flavor, and smooth texture.
2. Very good performance in storage trials.
3. Good tolerance to bacterial canker caused by *Pseudomonas syringae.*

BRIEF DESCRIPTION OF THE DRAWINGS

The accompanying photographic illustration shows typical specimens in full color of the foliage and fruit of the new variety 'Overtime.' The colors are a nearly true as is reasonably possible in a color representation of this type.

BOTANICAL DESCRIPTION

Figure 1:
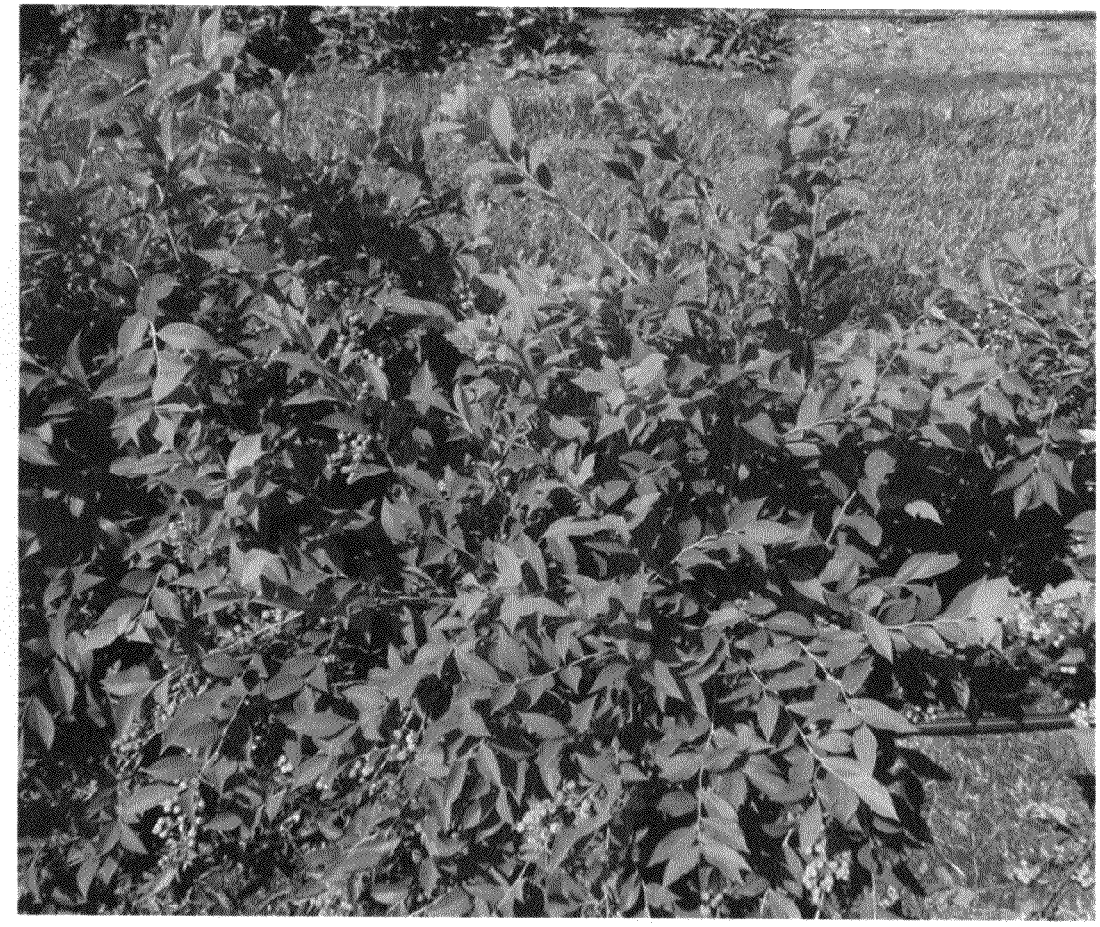
FIG. 1 is a photograph of the new variety 'Overtime.'
Figure 2:
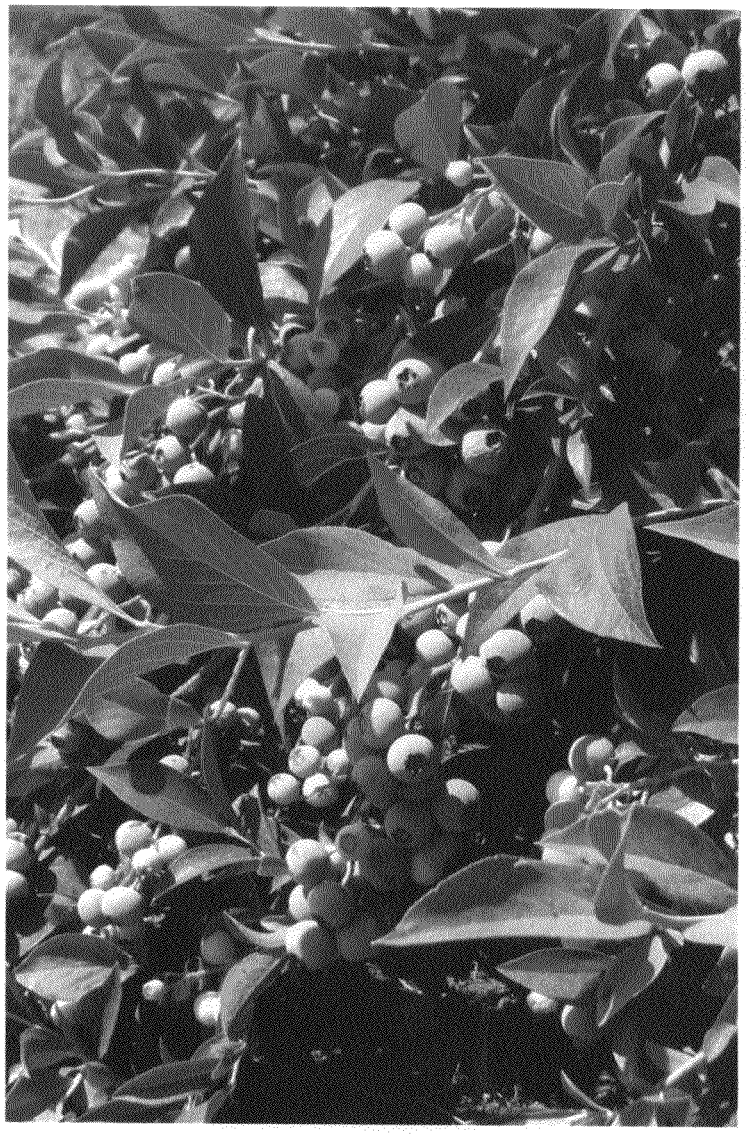
FIG. 2 is a photograph of the fruit of the new variety 'Overtime.'
Figure 3:
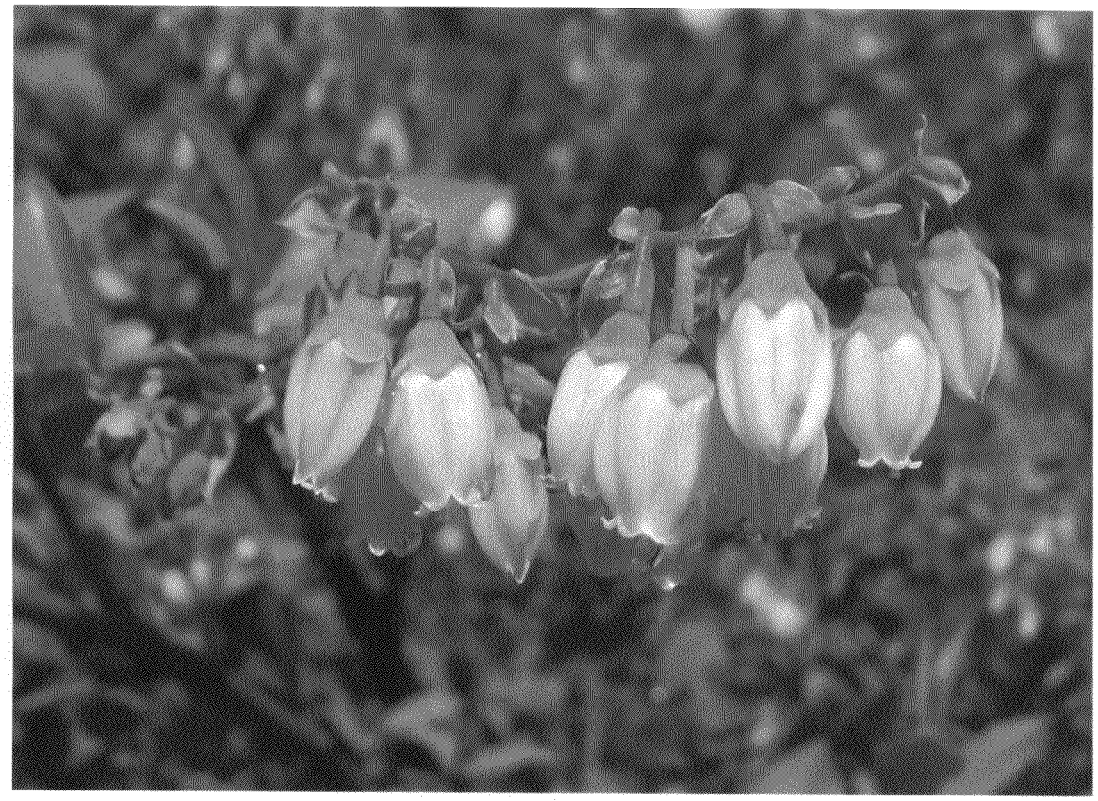
FIG. 3 is a photograph of the flowers of the new variety 'Overtime.'

The following detailed description sets forth the distinctive characteristics of 'Overtime.' The data which defines these characteristics was collected from asexual reproductions of the original selection. Dimensions, sizes, colors, and other characteristics are approximations and averages set forth as accurately as possible. The plant history was taken on plants approximately three years of age, and the descriptions relate to plants grown in the field in Lowell, Oreg. Color designations are from "The Pantone Book of Color" (by Leatrice Eiseman and Lawrence Herbert, Harry N. Abrams, Inc., Publishers, New York, 1990). Where the Pantone color designations differ from the colors in the photographs, the Pantone colors are accurate.

Classification:

*a. Family.*—Ericaceae.

*b. Genus.*—*Vaccinium.*

*c. Species.*—*virgatum.*

*d. Common name.*—Rabbiteye Blueberry.

Parentage:

*Female parent.*—'Centurion' (unpatented).

*Male parent.*—'Powderblue' (unpatented).

Market class: 'Overtime' is a commercial variety intended for the hand harvest fresh market.

PLANT

Plant size:

*a. Height of plant.*—Average of 32 inches on 4 year old plants.

*b. Canopy diameter.*—Average 30 inches on 4 year old plants.

Growth habit: Upright base, floppy structure.

Plant vigor: Vigorous.

Twigginess: Low.

Evergreenness: Deciduous.

Suckering: Moderate suckering.

Chilling requirement: Approximately 500-700 hours.

Cold hardiness: Estimated USDA hardiness zones 7-9.

Productivity: In Lowell, Oreg.

*a. On* 3 *yr old plants.*—0.8 lbs per plant, compared to 0.52 lbs per plant for 'Ocholockonee' plants of the same age, and 1.23 lbs per plant on 'Powderblue' plants of the same age.

*b. On* 4 *yr old plants.*—3.67 lbs per plant, compared to 5.35 lbs per plant for 'Ochlockonee' plants of the same age, and compared to 7.49 lbs per plant for 'Powderblue' plants of the same age.

Propagation: Easy to propagate from softwood cuttings.

Disease and pest resistance/susceptibility:

*a. Root rot* (*Phytophthora cinnamomi*).—Does not appear to be overly susceptible.

*b. Phomopsis twig blight* (*Phomopsis vaccinii*).—Does not appear to be overly susceptible.

*c. Stem blight* (*Botryosphaeria spp*).—Undetermined.

*d. Botryosphaeria stem canker* (*Botryosphaeria corticis*).—Undetermined.

*e. Bacterial cane canker* (*Pseudomonas syringae*).—Does not appear to be overly susceptible.

*f. Botrytis blight* (*Botrytis cinerea*).—Does not appear to be overly susceptible.

*g. Leaf spot* (*Septoria spp.*).—Does not appear to be overly susceptible.

*h. Leaf rust* (*Naohidemyces vaccinii*).—Does not appear to be overly susceptible.

*i. Bud mites* (*Acalatus vaccinii*).—Undetermined.

Disease survival: Good.

WOOD

Texture:

*a. Surface texture new wood.*—Smooth.

*b. Surface texture* 1 *yr Wood.*—Smooth.

*c. Surface texture* 3 *yr wood.*—Rough.

Color:

*a. Color new wood.*—Pantone color Parrot Green 15-0341.

*b. Color rough bark* 1 *yr.*—Pantone color Moss 16-0532.

*c. Color rough bark* 3 *yr.*—Pantone colors Aztec 18-1130 and Chinchilla 17-1109.

LEAVES

Internode length: Average of 19.41 mm.

Leaf dimensions:

*a. Leaf length.*—Average 78.56 mm.

*b. Leaf width.*—Average 29.25 mm.

Leaf shape: Elliptical with acute base and apex.

Leaf margin: Serrulate.

Leaf color:

*a. Upper leaf surface.*—Pantone colors Mature leaf — Grasshopper 18-0332.

*b. Upper leaf surface new leaves.*—Piquant Green 17-0235, with Maroon 18-1619 at top edge.

*c. Lower leaf surface.*—Pantone color Peridot 17-0336.

Fall foliage color: Pantone Holly Berry 17-1633.

Pubescence:

*a. Pubescence upper leaf surface.*—Absent.

*b. Pubescence lower leaf surface.*—Absent.

*c. Pubescence leaf margins.*—Absent.

Petiole:

*a. Petiole length.*—Average 1.70 mm.

*b. Petiole color.*—Pantone colors Sweet Pea 15-0531 and Cranberry 17-1545.

*c. Petiole surface texture.*—Smooth.

Leafing vs flowering: Flower bud break occurs prior to vegetative bud break in Lowell, Oreg. Flowers persist during initial vegetative growth period.

FLOWERS

Flower arrangement: Flowers arranged alternately along branch.

Fragrance: Faint, sweet.

Immature flower color: Pantone colors White Swan 12-000 and Dusty Rose 17-1718.

Anther:

*a. Anther length.*—Average of 3.98 mm.

*b. Anther color.*—Pantone color Burnt Orange 16-1448.

Flower shape: Cylindrical.

Pollen:

*a. Pollen staining.*—Staining with 2% acetocarmine dye, approximately 95% viable.

*b. Pollen abundance.*—Medium.

*c. Pollen color.*—Pantone color Pale Banana 12-0824.

Flower length: Average of 11.12 mm.

Corolla:

*a. Corolla length*.—Average of 8.2 mm.

*b. Corolla diameter*.—Average of 6 mm.

*c. Corolla aperture*.—Average of 2.56 mm.

*d. Corolla color*.—Pantone color Pastel Parchment 11-0603.

*e. Corolla texture*.—Smooth.

Style length: Average of 8.4 mm.

Calyx:

*a. Calyx diameter*.—Average of 3.53 mm.

*b. Calyx surface*.—Smooth.

*c. Calyx color*.—Pantone color Green Olive 17-0535; Wild Rose 16-1715, and Lilas 16-1708.

Pistil color: Pantone color Mellow Green 12-0426.

Pedicel:

*a. Pedicel color*.—Pantone color Green Olive 17-0535; Wild Rose 16-1715, and Lilas 16-1708.

*b. Pedicel length flower*.—Variable, average of 9.6 mm.

Peduncle:

*a. Peduncle color*.—Pantone color Raw Sienna 17-1436 and Red Ochre 18-1442.

*b. Peduncle length flower*.—Variable, average of 7.17 mm.

Flowering period: In Lowell, Oreg. begins flowering in early May, reaches approximately 50% bloom in mid-May and continues flowering through late May to early June.

Flowering cluster: Loose.

Number flowers: Average of 4-7 flowers per cluster.

Self-compatibility: Moderate. On average, 48% of self-pollinated flowers reach maturity.

Stigma location: Average 0.61 mm above lip of corolla.

Average inflorescence size: 27.97 mm.

FRUIT

Mean harvest date: August 28.

Mean date last pick: September 15.

Calyx:

*a. Calyx aperture*.—Average of 4.83 mm.

*b. Calyx lobes*.—5 indistinct lobes.

*c. Calyx depth*.—Average 0.76 mm.

Berry cluster: Loose.

Berry pedicel:

*a. Length*.—Variable, average of 10.44 mm.

*b. Surface texture*.—Smooth.

Berry peduncle:

*a. Length*.—Variable, average of 28.88 mm.

*b. Surface texture*.—Smooth.

Berries per cluster: Average of 5-7 per cluster.

Berry detachment: Moderately easy.

Berry weight: Average of 1.61 g per berry, compared to Ochlockonee plants of the same age, which had an average of 1.51 g per berry, and Powderblue plants of the same age, which had an average of 1.04 g per berry.

Berry height: Average of 13.07 mm.

Berry width: Average of 16.88 mm.

Berry shape: Round.

Berry skin color:

*a. Immature berry color*.—Pantone color Parrot Green 15-0341.

*b. Berry skin color on plant*.—Pantone color Gray Dawn 14-4106.

*c. Berry skin color after harvest*.—Pantone color Chicory 16-4013.

*d. Berry skin color after polishing*.—Pantone color India Ink 19-4019.

Berry wax: Heavy, persistent wax.

Berry flesh color: Pantone color Vanilla 12-0712.

Pedicel scar: Small and dry, average of 1.56 mm in diameter.

Berry firmness: Firm.

Berry flavor: Sweet.

Berry texture: Firm.

SEEDS

Seed color: Pantone color Copper Brown 18-1336.

Seed length: Average of 2.07 mm.

Seed width: Average of 1.24 mm.

Seed weight: Average of 0.6 mg.

Quantity seeds per berry: Average of 26 seeds per berry.

TABLE 1

DISTINGUISHING FEATURES FROM FEMALE PARENT 'CENTURION'

| Name of maternal parent | Characteristic(s) in which the candidate variety differs from the maternal parent | Describe the expression of the characteristic for the maternal parent | Describe the expression of the characteristic for 'Overtime' |
|---|---|---|---|
| Centurion | Color of new wood | Red/green | Green |
| Centurion | Time of fruit ripening (one year shoots) | Mid-late | Very late |

The invention claimed is:

1. A new and distinct variety of blueberry plant named 'Overtime,' substantially as illustrated and described herein.

* * * * *